(12) United States Patent
Harding et al.

(10) Patent No.: US 7,713,392 B2
(45) Date of Patent: May 11, 2010

(54) TEST STRIP CODING AND QUALITY MEASUREMENT

(75) Inventors: Ian Harding, Somerville, MA (US); Sridhar Iyengar, Salem, NH (US); Baoguo Wei, Salem, NH (US); Steven Diamond, Somerville, MA (US); Martin Forest, Nashua, NH (US)

(73) Assignee: Agamatrix, Inc., Salem, NH (US)

( * ) Notice: Subject to any disclaimer, the term of this patent is extended or adjusted under 35 U.S.C. 154(b) by 1263 days.

(21) Appl. No.: 10/907,805

(22) Filed: Apr. 15, 2005

(65) Prior Publication Data

US 2006/0231417 A1   Oct. 19, 2006

(51) Int. Cl.
    *G01N 27/327* (2006.01)
(52) U.S. Cl. .............. 204/403.02; 204/403.01; 204/403.04; 205/777.5
(58) Field of Classification Search ............. 204/403.02
    See application file for complete search history.

(56) References Cited

U.S. PATENT DOCUMENTS

| 5,160,278 | A | 11/1992 | Johnson |
| 2003/0116447 | A1 | 6/2003 | Surridge et al. |
| 2003/0146110 | A1 | 8/2003 | Karinka et al. |
| 2003/0159945 | A1* | 8/2003 | Miyazaki et al. ......... 205/777.5 |
| 2003/0178322 | A1 | 9/2003 | Iyengar et al. |
| 2004/0045821 | A1* | 3/2004 | Cui et al. ............ 204/403.02 |
| 2004/0086423 | A1 | 5/2004 | Wohlstadter et al. |
| 2004/0182703 | A1 | 9/2004 | Bell et al. |
| 2005/0069892 | A1 | 3/2005 | Iyengar et al. |
| 2005/0098433 | A1 | 5/2005 | Gundel |
| 2005/0098434 | A1 | 5/2005 | Gundel et al. |

FOREIGN PATENT DOCUMENTS

| WO | 0171328 A1 | 9/2001 |
| WO | WO 03/060154 A2 | 7/2003 |
| WO | WO 03/069304 A2 | 8/2003 |
| WO | WO 2005/022143 | 8/2004 |

* cited by examiner

*Primary Examiner*—Harry D. Wilkins, III
*Assistant Examiner*—Bryan D. Ripa
(74) *Attorney, Agent, or Firm*—Larson & Anderson, LLC

(57) ABSTRACT

A test strip and analytical apparatus have pin connections permitting the definition of geographic regions or of particular customers. A test strip made for use in a particular region or for a particular customer will have pin connections matching features of the apparatus made for use in that region or by that customer. Insertion of the strip into the apparatus does not merely turn on the apparatus, but provides the regional or customer coding. Analog switches within the apparatus allow coding of a larger number of distinct regions or customers than would otherwise be possible, all without degrading the quality of the measurements made of the fluid being tested. Conductive paths in the strips permit testing the strips during manufacture so as to detect quality lapses regarding the printing or deposition of the paths.

6 Claims, 4 Drawing Sheets

|      | 13    | 12    | 11    | 10    | 9     | 8     |
|------|-------|-------|-------|-------|-------|-------|
| PIN1 | C     | -     | C     | -     | C     | SD1/C |
| PIN2 | SD2   | SD2   | GND/W | GND/C | SD2   | GND/C |
| PIN3 | SD1/W | SD1/C | SD1/W | SD1/C | -     | -     |
| PIN4 | GND/W | GND/C | SD2   | SD2   | GND/W | SD2   |
| PIN5 | -     | W     | -     | W     | SD1/W | W     |

|     | 13  | 12  | 11  | 10  | 9   | 8   |
|-----|-----|-----|-----|-----|-----|-----|
| JP1 | 2-3 | 2-3 | 2-3 | 2-3 | 2-4 | 1-2 |
| JP2 | 2-3 | 2-3 | 1-2 | 1-2 | 2-3 | 1-2 |
| JP3 | 1-2 | 1-2 | 2-3 | 2-3 | 1-2 | 2-3 |
| JP4 | 2-3 | 2-4 | 2-3 | 2-4 | 2-4 | 2-4 |
| JP5 | 1-2 | 2-3 | 1-2 | 2-3 | 1-2 | 1-2 |

Fig.5

TEST STRIP CODING AND QUALITY MEASUREMENT

BACKGROUND

The invention relates to a system for analyzing a sample using an electrochemical cell. The electrochemical cell is provided in a test strip. The test strip is elongated and has the cell at one end (sometimes called the "distal" end) and has a connection region at the other end (sometimes called the "proximal" end). The connector region is shaped to plug into a connector on an apparatus. The apparatus contains electronic circuitry for applying signals to the cell and for monitoring signals received from the cell.

The test strip is made up of layers. In an exemplary embodiment the layers are as described in U.S. patent application No. 60/521,555 filed May 21, 2004, which application is incorporated herein by reference for all purposes. An elongated substrate or carrier provides mechanical rigidity and support. Deposited or painted onto the substrate are conductive paths such as those shown in FIG. 1 at locations 10, 11, 13. FIG. 1 shows a plan view of one of the layers of a strip. These paths may be gold or silver or palladium or conductive carbon. The electrochemical reaction cell is built up in area 12 in FIG. 1. Area 10 defines a "working" electrode of the reaction cell, and the cell also includes a "counter" electrode omitted for clarity in FIG. 1.

Turning ahead to FIG. 2, what is seen is a cross section in a plane that extends along the length of the elongated strip and that is perpendicular to the plane portrayed in FIG. 1. Conductive paths 11, 13, 10 may be seen in FIG. 2 and these are the same paths 11, 13, 10 shown in FIG. 1. Reagent material 14 defines the reaction cell mentioned above, which is in area 12. What may be seen in FIG. 2 (and what was omitted for clarity in FIG. 1) is a conductive path 15, deposited in a plane that is parallel and above the plane of FIG. 1. This path 15, together with other geometry, defines the counter electrode of the reaction cell. Thus the material 14 lies between the working electrode and the counter electrode but (in an exemplary embodiment) does not fill the space between the two electrodes. The dry reagent does not "touch" the counter electrode.

The path 15 (not visible in FIG. 1) extends far enough to overlap with path 11 (visible in FIG. 1). A crossover area 16 is constructed providing an electrically conductive connection between the path 11 and the path 16. It will be appreciated that the structure of the strip typically includes insulating elements and adhesive elements that are omitted for clarity in FIGS. 1 and 2, as well as physical features that provide a place where a fluid of interest (such as blood) may be introduced. When the fluid is introduced, it enters the reaction cell lying between conductive paths 10 and 15 in FIG. 2. The apparatus passes signals into the strip by means of the above-mentioned connector and through paths 10, 11, and 16 to the reaction cell. Returned signals permit the apparatus to analyze particular properties of the fluid. In an exemplary embodiment the fluid is human blood, the reagent material 14 includes a glucose oxidase, and the property being measured is the glucose content of the blood. (More generally instead of glucose oxidase any glucose-responsive enzyme might be employed.)

Exemplary methods and apparatus for such analysis are described in PCT publications WO 2005/022143, WO 03/069304, and WO 2003/060154, each of which is hereby incorporated herein by reference for all purposes.

It would be extremely desirable to devise features of a test strip which would permit testing of the strip to find out whether the conductive paths are being laid down correctly.

One problem with many test strip designs is that testing of particular conductive paths risks damaging the paths. With such designs, the very act of testing poses a risk of making the strip less reliable. Destructive testing then leads to lower manufacturing yields. This is an undesirable state of affairs.

It would also be extremely desirable to devise features of a test strip and of the associated analytical apparatus which would permit defining particular test strips as having been made for use in particular geographic regions or for specific customers. Then, in a way which brings to mind the regional coding of DVDs (digital video disks) and DVD players, a strip made for use in a particular region or for a particular customer would work only with an apparatus made for use in that region.

Finally it would be desirable to have a structure of conductors that helps to control the printing of the reagent so that it deposits in the right place.

SUMMARY OF THE INVENTION

A test strip and analytical apparatus have pin connections permitting the definition of geographic regions or of particular customers. A test strip made for use in a particular region or for a particular customer will have pin connections matching features of the apparatus made for use in that region or by that customer. Insertion of the strip into the apparatus does not merely turn on the apparatus, but provides the regional or customer coding. Analog switches within the apparatus allow coding of a larger number of distinct regions or customers than would otherwise be possible, all without degrading the quality of the measurements made of the fluid being tested. Conductive paths in the strips permit testing the strips during manufacture so as to detect quality lapses regarding the printing or deposition of the paths.

DESCRIPTION OF THE DRAWING

The invention will be described with respect to a drawing in several figures.

FIG. 5 shows six strip configurations in addition to those shown in FIG. 1.

DETAILED DESCRIPTION

Figure 1:
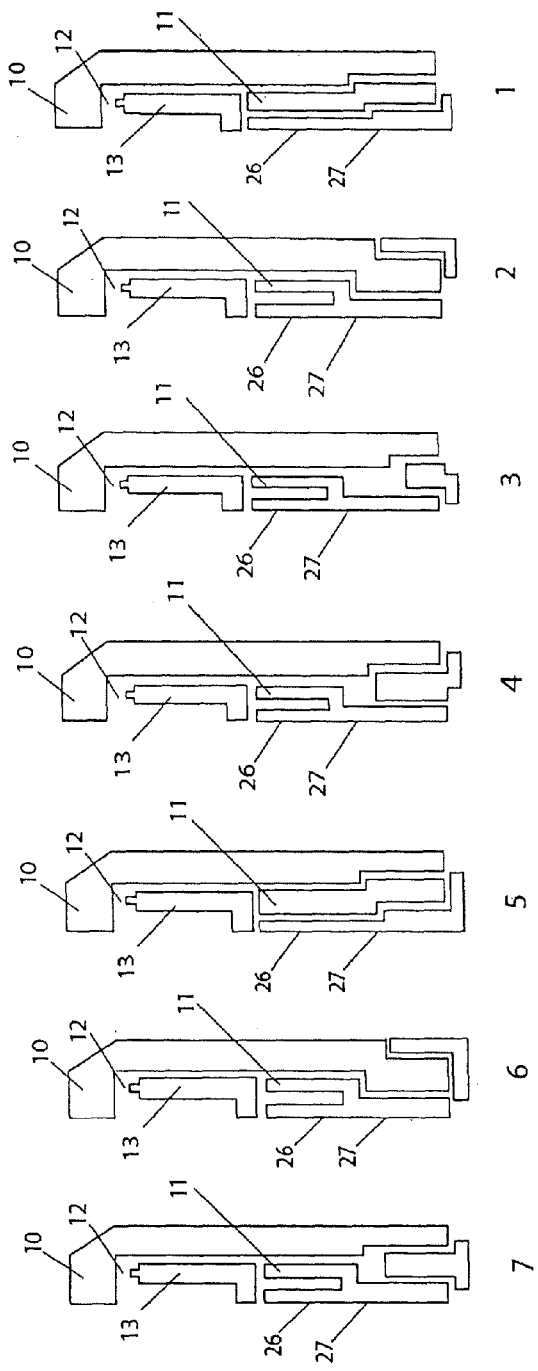
FIG. 1 shows seven strip configurations in plan view, and also shows pin assignments and jumper assignments.

FIG. 1 shows seven strip configurations in plan view, and also shows pin assignments and jumper assignments. Working electrode areas 10 may be seen as well as counter electrode conduction paths 11. Each strip is elongated with its distal end toward the electrode areas 10 and its proximal end toward the connector area at the other end (toward the bottom of the figure in FIG. 1).

For each of these configurations, particular pin assignments must be made. The pin assignments appear toward the top of FIG. 1. In each case "C" means the counter electrode, "W" means the working electrode, GND means ground, SD1 means strip detect 1, and SD2 means strip detect 2. Thus for example in the case of configuration 4, it is communicated that the counter electrode connects to the analytical apparatus through connector pin 1, the working electrode connects to the apparatus through pin 5, and so on. This can then be used in connection with circuitry such as that described in copending U.S. application Ser. No. 10/907,790, which application is incorporated herein by reference for all purposes.

Toward the bottom of FIG. 1 is a table showing jumpers to be installed in the apparatus so that the apparatus will match a particular strip configuration.

Figure 2:
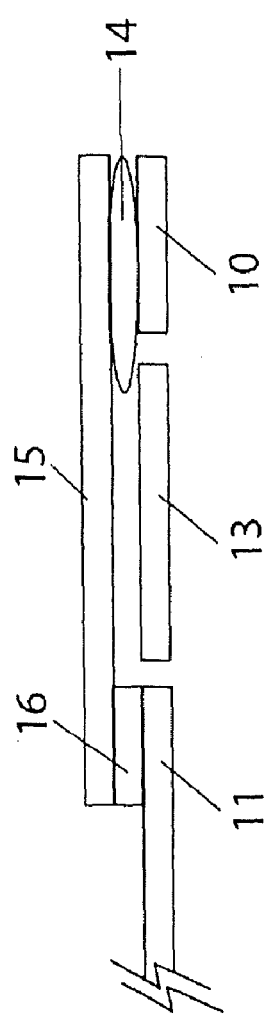
FIG. 2 is a cross-sectional view of a typical strip of FIG. 1.

FIG. 2 is a cross-sectional view of a typical strip of FIG. 1, discussed at some length above.

Figure 3:
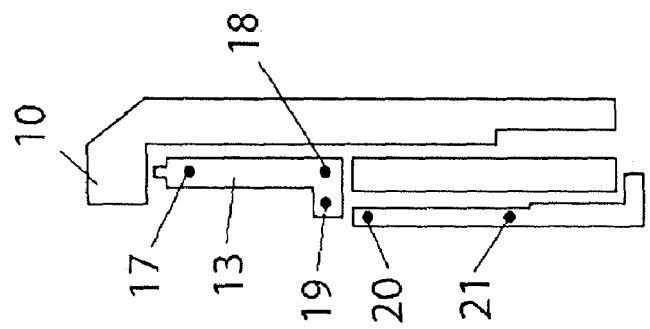
FIG. 3 identifies points in a strip that is under manufacture, which points may be used for destructive testing if desired.

FIG. 3 identifies points in a strip that is under manufacture, which points may be used for destructive testing if desired. Experience shows that the painting or deposition of conductive material during manufacture (for example paths 11, 13, 10, 15) can sometimes turn out badly. For example some manufacturing defects can lead to gapping or abnormal thickness (too thick or too thin) in the laid-down conductive paths. Some such defects sometimes manifest themselves only in a "Y" direction (from proximal to distal) while other defects manifest themselves in an X direction (perpendicular to the Y direction). Another way to say this is that the screen printing process is anisotropic.

The conductive path 13, for example, permits pressing probes into the path at 17 and 18 to test for defects in the Y direction. Probes can be pressed into positions 19 and 18 as well, which will test for defects in the X direction. Such tests may damage the path 13 but if they do, this does not interfere with or degrade the signals to and from the reaction cell.

If the path containing points 20 and 21 is not otherwise in use, then the test equipment could be used at those two points, again without degrading the signals to and from the reaction cell.

Returning briefly to FIG. 1, configuration 7 shows two positions 26, 27. These positions are part of the path 11, in the sense of having been printed all at the same time. But importantly, the part of the path 11 that contains 26 and 27 can be freely used for testing without jeopardizing the later ability to collect the signals, since that part is not on a "conductive path" to the conductor 16. Stated differently the testing areas such as points 26 and 27 are not in a conduction path for purposes of analysis.

Stated differently, in one embodiment a planar test strip is elongated for a length along a first axis, the strip having an electrochemical analysis cell at one axial end and a connection region at the other axial end, the strip made up of at least a first layer. The first layer has deposited thereupon at least one conductor extending from the connection region to the electrochemical cell, the conductor having a first portion which is not a conductive path for analysis. The first portion extends along the axis for at least one-fifth of the length of the strip. First and second test probes may be applied to the first portion, the first and second test probes separated by at least one-fifth of the length of the strip.

Furthermore, the strip has a width, and the conductor has a second portion which is not a conductive path for analysis, the second portion extending perpendicular to the axis for at least one-fifth of the width of the strip. Third and fourth test probes may be applied to the second portion, the third and fourth test probes separated by at least one-fifth of the width of the strip. The third and fourth probes can be the same as the first and second probes, or can be different.

Figure 4:
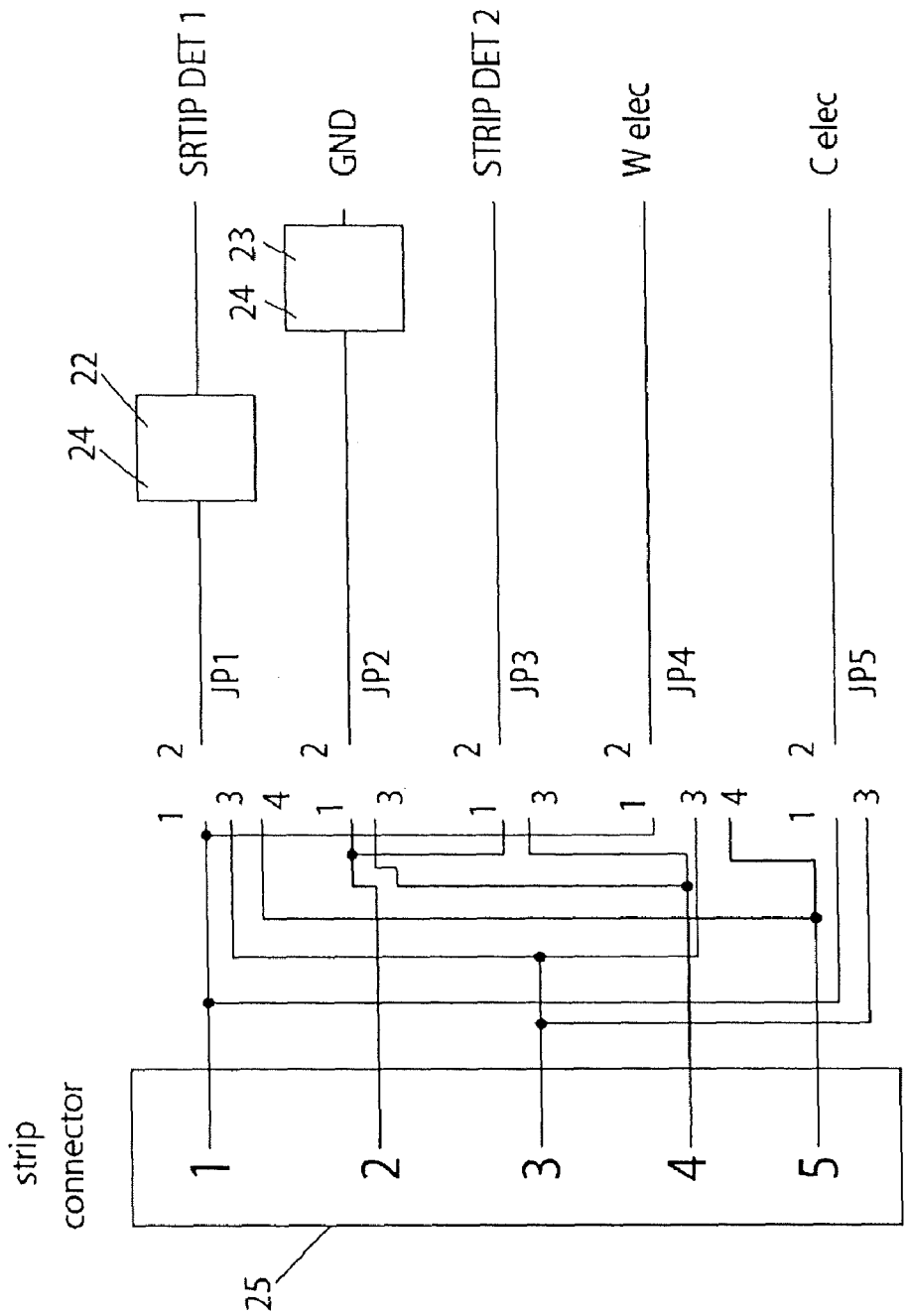
FIG. 4 shows a strip connector for the analytical apparatus, as well as programming jumpers and analog switches.

FIG. 4 shows a strip connector for the analytical apparatus, as well as programming jumpers and analog switches. The jumpers to be installed are those shown in FIG. 1 or 5. Analog switches 22, 23 may be seen, about which more will be said below. The strip connector 25 (to the left in FIG. 4) is what receives a test strip. The right side of FIG. 4 lists five signals passed to the microcontroller of the apparatus. A "detection done" signal 24 permits opening the two switches 22, 23 when the apparatus has finished detecting the strip.

Omitted for clarity in FIG. 4 is a microcontroller which receives the various signals depicted in FIG. 4. It may use an analog-to-digital convertor to analyze the signals, or a general-purpose I/O port, or a simple comparator. In the case of a general-purpose I/O port, there can be a pullup resistor.

The jumpers in FIG. 4 are preferably zero-ohm resistors which are surface-mounted by automatic pick-and-place equipment.

It should be noted that the arrangement of FIG. 4 has jumper fields (or switch contacts) in which the "common" contact is to the right in FIG. 4 and the selected contacts are to the left in FIG. 4. It will then be appreciated that the "common" contacts could be to the left in FIG. 4 with the selected contacts to the right in FIG. 4.

FIG. 5 shows six strip configurations in addition to those shown in FIG. 1. In each of the cases the strip-detect function is shared with one or more of the electrode lines. While this makes the circuit design more complicated, it permits defining a larger number of regions.

In the case of configuration 8, for example, the counter electrode is shared with the strip-detect 1 and ground detection signals.

Once the meter (analytical apparatus) has detected the strip, the meter breaks the shared connection by asserting "detection done" (line 24 in FIG. 4). This opens switches 22, 23. The result is that the electrode signals are able to be passed henceforth without adding interference.

It should be appreciated that in an exemplary embodiment, the meter does not merely detect a strip, but specifically detects which connector pins are connected (within the strip) to other connector pins. Furthermore, the meter even more specifically checks to make sure that pins which are not supposed to be connected to anything else (within the strip) are in fact not connected to anything else.

Stated differently, if a strip is inserted, the meter may detect it (will "wake up"), but then if the jumper configuration of the meter fails to match the within-the-strip connections, then the meter will not proceed with analysis but will instead annunciate the mismatch.

Thus, the meter checks not only that each pin that is supposed to be connected to some other pin is actually connected, but it also checks that any pin that is not supposed to be connected is actually not connected to anything else. The check may be termed an "if and only if" in the sense that the match is only satisfied if the correct pins are connected while the other pins that are not supposed to be connected are not connected.

In one embodiment, then, the meter determines whether predefined first and second pins of the strip are connected, defining a first finding, and determines whether a predefined third pin is not connected to either of the first and second pins, defining a second finding, and performs the analysis only in the event that the first and second findings are in the affirmative.

It will be further appreciated that it is possible to use varying resistance of various traces in the strip as a way of increasing the number of distinct strips that can be distinguished electrically.

The functionality described here is thus much more than a mere "strip detect" functionality.

Another aspect of the invention may be seen in connection with the reagent absorptive pad 12, which can be seen in FIG. 1. The reagent absorptive pad 12 has the salutary effect during manufacture that it helps to ensure that the reagent 14 is laid down properly. The reagent 14 is printed to the conductor 10 and to the absorptive pad 12. The reagent 14 sticks to these two conductors 10, 12 and thus is deposited in a reliable way.

Thus in one embodiment there is a planar test strip elongated for a length along a first axis, the strip comprising at least first, second, and third planar layers, the second planar layer lying between the first and third planar layers, the strip having an electrochemical analysis cell at one axial end and a connection region at the other axial end, the first layer having deposited thereupon a first conductor extending from the connection region to the electrochemical cell, the first layer also having deposited thereupon a second conductor extending nearby to but not in conductive relationship to the first conductor, the strip further comprising an electrochemical reagent deposited upon the first layer, the reagent extending to lie atop a portion of the first conductor and extending to lie atop a portion of the second conductor, the second conductor not in conductive relationship to the connection region.

A method used with such a planar test strip comprises the steps of depositing upon the first layer a first conductor extending from the connection region to the electrochemical cell, depositing upon the first layer a second conductor extending nearby to but not in conductive relationship to the first conductor, the second conductor not in conductive relationship to the connection region; and depositing upon the first layer an electrochemical reagent, the reagent extending to lie atop a portion of the first conductor and extending to lie atop a portion of the second conductor.

Those skilled in the art will have no difficulty devising myriad obvious improvements and variations, all of which are intended to fall within the scope of the invention as defined by the claims that follow.

What is claimed is:

1. A planar test strip elongated for a length along a first dimension parallel to a first axis and having a second dimension corresponding to the width of the strip, the strip having an electrochemical analysis cell at one axial end and a connection region at the other axial end, the strip made up of at least a first layer; the first layer having deposited thereupon at least one conductor divided into a plurality of conductively isolated portions, including at least one portion extending from the connection region to the electrochemical cell to provide a conductive path for analysis, and a second portion which is not a conductive path for analysis extending from the connector region towards the electrochemical cell but which does not make contact with sample in the electrochemical cell; wherein said second portion extends in the first or second dimension for at least one-fifth of the dimension.

2. The strip of claim 1, wherein the conductor has a second portion, separate from the first conductive portion, which is not a conductive path for analysis and which does not make contact with sample in the electrochemical cell; said second portion extending in the other of the first and second dimension for at least one-fifth of the second dimension.

3. The test strip of claim 1, wherein the first portion extends along the length the axis for at least one-fifth the length of the strip.

4. The test strip of claim 1, wherein the first portion extends across the width of the strip for at least one-fifth the width.

5. A planar test strip elongated for a length along a first axis, the strip comprising at least first, second, and third planar layers, the second planar layer lying between the first and third planar layers; the strip having an electrochemical analysis cell at one axial end and an exposed connection region at the other axial end, said exposed connection region being defined by an end edge of the second and/or third planar layers; the first layer having deposited thereupon a first conductor extending from the exposed connection region to the electrochemical cell, the first layer also having deposited thereupon a second conductor extending nearby to but not in conductive relationship to the first conductor; the strip further comprising an electrochemical reagent deposited upon the first layer, the reagent extending to lie atop a portion of the first conductor and extending to lie atop a portion of the second conductor; the second conductor not in conductive relationship to the exposed connection region.

6. A method of making a planar test strip elongated for a length along a first axis, the strip comprising at least first, second, and third planar layers, the second planar layer lying between the first and third planar layers; the strip having an electrochemical analysis cell at one axial end and an exposed connection region at the other axial end, said exposed connection region being defined by an end edge of the second and/or third planar layers; the method comprising the steps of depositing upon the first layer a first conductor extending from the exposed connection region to the electrochemical cell, depositing upon the first layer a second conductor extending nearby to but not in conductive relationship to the first conductor, the second conductor not in conductive relationship to the exposed connection region; and depositing upon the first layer an electrochemical reagent, the reagent extending to lie atop a portion of the first conductor and extending to lie atop a portion of the second conductor.

* * * * *